(12) United States Patent  (10) Patent No.: US 8,721,559 B2
Peterson et al.  (45) Date of Patent: May 13, 2014

(54) NON-INVASIVE METHOD AND DEVICE FOR MEASURING CARDIAC OUTPUT

(75) Inventors: Stephen C. Peterson, Salt Lake City, UT (US); Tomasz J. Petelenz, Salt Lake City, UT (US); Stephen C. Jacobsen, Salt Lake City, UT (US)

(73) Assignee: Raytheon Company, Waltham, MA (US)

( * ) Notice: Subject to any disclaimer, the term of this patent is extended or adjusted under 35 U.S.C. 154(b) by 799 days.

(21) Appl. No.: 12/348,842

(22) Filed: Jan. 5, 2009

(65) Prior Publication Data

US 2010/0022900 A1  Jan. 28, 2010

Related U.S. Application Data

(60) Provisional application No. 61/010,035, filed on Jan. 4, 2008.

(51) Int. Cl.
*A61B 5/02* (2006.01)
*A61B 5/05* (2006.01)

(52) U.S. Cl.
CPC .................................... *A61B 5/05* (2013.01)
USPC ............................................ 600/526; 607/65

(58) Field of Classification Search
USPC ................................ 600/526; 607/32, 60, 65
See application file for complete search history.

(56) References Cited

U.S. PATENT DOCUMENTS 3,572,316 A  3/1971  Vogelman et al.
(Continued)

FOREIGN PATENT DOCUMENTS

| WO | WO2007/033270 | 3/2007 |
| WO | WO2008/036396 | 3/2008 |
| WO | WO 2008036404 A2 * | 3/2008 |
| WO | WO2008/148040 | 12/2008 |

OTHER PUBLICATIONS

Staderini E M et al., "Optimization criteria in the design of medical UWB radars in compliance with regulatory masks" Biomedical Circuits and Systems Conference, IEEE, Nov. 27, 2007 pp. 53-58.

(Continued)

*Primary Examiner* — Kennedy Schaetzle
*Assistant Examiner* — Erica Lee
(74) *Attorney, Agent, or Firm* — Thorpe North & Western LLP

(57) ABSTRACT

A system comprising a housing containing a signal generator coupled to an antenna and a dielectric material disposed about the antenna. The device is adapted to generate and direct a plurality of signals towards the heart of the person and measure a magnitude of a signal returned from the heart. The device further comprises a processor to compare differences between a magnitude of a signal propagated and the magnitude of the signal returned off the heart and determine a signal frequency having a maximum return loss value based on those differences. The processor also estimates a change in the amplitude of motion of a portion of a wall of the heart based on the differences between the magnitude of the signal propagated by the device and the magnitude of the signal returned off of the portion of the heart.

23 Claims, 13 Drawing Sheets

(56) References Cited

U.S. PATENT DOCUMENTS

| | | | |
|---|---|---|---|
| 3,646,606 | A | 2/1972 | Buxton et al. |
| 3,846,704 | A | 11/1974 | Bessette |
| 3,972,320 | A | 8/1976 | Kalman |
| 4,129,125 | A | 12/1978 | Lester et al. |
| 4,204,549 | A | 5/1980 | Paglione |
| 4,240,445 | A | 12/1980 | Iskander |
| 4,270,547 | A | 6/1981 | Steffen et al. |
| 4,312,358 | A | 1/1982 | Barney |
| 4,331,154 | A | 5/1982 | Broadwater et al. |
| 4,341,227 | A | 7/1982 | Turner |
| 4,397,313 | A | 8/1983 | Vaguine |
| 4,446,874 | A | 5/1984 | Vaguine |
| 4,488,559 | A | 12/1984 | Iskander |
| 4,494,553 | A | 1/1985 | Sciarra et al. |
| 4,531,527 | A | 7/1985 | Reinhold, Jr. et al. |
| 4,608,994 | A | 9/1986 | Ozawa et al. |
| 4,633,875 | A | 1/1987 | Turner |
| 4,819,860 | A | 4/1989 | Hargrove |
| 4,841,990 | A | 6/1989 | Kikuchi |
| 4,867,170 | A | 9/1989 | Takahashi |
| 4,867,442 | A | 9/1989 | Matthews |
| 4,909,260 | A | 3/1990 | Salem et al. |
| 4,926,868 | A | 5/1990 | Larsen |
| 4,958,638 | A | 9/1990 | Sharpe |
| 4,966,154 | A | 10/1990 | Cooper et al. |
| 4,991,585 | A | 2/1991 | Mawhinney |
| 5,022,402 | A | 6/1991 | Schieberl et al. |
| 5,025,795 | A * | 6/1991 | Kunig ............... 600/526 |
| 5,027,824 | A | 7/1991 | Dougherty et al. |
| 5,027,829 | A | 7/1991 | Larsen |
| 5,062,432 | A | 11/1991 | James |
| 5,090,423 | A | 2/1992 | Matsuda |
| 5,101,836 | A | 4/1992 | Lee |
| 5,148,002 | A | 9/1992 | Kuo et al. |
| 5,153,584 | A | 10/1992 | Engira |
| 5,178,151 | A | 1/1993 | Sackner |
| 5,186,181 | A | 2/1993 | Franconi |
| 5,228,449 | A | 7/1993 | Christ et al. |
| 5,263,491 | A | 11/1993 | Thrrnton |
| 5,284,144 | A | 2/1994 | Delannoy |
| 5,335,664 | A | 8/1994 | Nagashima |
| 5,373,301 | A | 12/1994 | Bowers |
| 5,404,877 | A * | 4/1995 | Nolan et al. ............ 600/484 |
| 5,416,468 | A | 5/1995 | Baumann |
| 5,423,322 | A | 6/1995 | Clark |
| 5,442,369 | A | 8/1995 | Voorhies |
| 5,515,858 | A | 5/1996 | Myllymaki |
| 5,544,651 | A | 8/1996 | Wilk |
| 5,654,723 | A | 8/1997 | Craven |
| 5,683,382 | A * | 11/1997 | Lenihan et al. ............ 606/33 |
| 5,693,074 | A | 12/1997 | Ferek-Petric |
| 5,724,025 | A | 3/1998 | Tavori |
| 5,734,353 | A | 3/1998 | Voorhies |
| 5,748,002 | A | 5/1998 | Scott |
| 5,766,208 | A * | 6/1998 | McEwan ............... 600/595 |
| 5,769,879 | A | 6/1998 | Richards |
| 5,771,001 | A | 6/1998 | Cobb |
| 5,778,882 | A | 7/1998 | Raymond et al. |
| 5,807,257 | A | 9/1998 | Bridges |
| 5,829,437 | A | 11/1998 | Bridges |
| 5,841,288 | A | 11/1998 | Meaney |
| 5,861,019 | A * | 1/1999 | Sun et al. ............ 607/60 |
| 5,952,978 | A | 9/1999 | Voorhies |
| 6,064,903 | A | 5/2000 | Riechers et al. |
| 6,233,479 | B1 | 5/2001 | Haddad et al. |
| 6,368,286 | B1 | 4/2002 | Whitman et al. |
| 6,522,196 | B1 | 2/2003 | Poggi et al. |
| 6,595,928 | B2 | 7/2003 | Mansy et al. |
| 6,829,501 | B2 | 12/2004 | Nielsen et al. |
| 6,903,692 | B2 | 6/2005 | Kivekas et al. |
| 7,450,746 | B2 | 11/2008 | Yang et al. |
| 7,450,986 | B2 | 11/2008 | Nguyen et al. |
| 2004/0249258 | A1 | 12/2004 | Tupin, Jr. et al. |
| 2005/0124901 | A1 | 6/2005 | Misczynski et al. |
| 2011/0144508 | A1 * | 6/2011 | Blomqvist et al. ............ 600/508 |

OTHER PUBLICATIONS

Staderini, Enrico M., "UWB radars in medicine", IEEE Aerospace and Electronic Systems Magazine, Jan. 1, 2002, pp. 13-18, vol. 17, No. 1.

Newman, David et al., The non-invasive assessment of stroke volume and cardiac output by impedance cardiography: A review, Aviation, Space and Environmental Medicine, Aerospace Medical Association, Aug. 1, 1999, pp. 780-789, vol. 70 No. 8.

www.biopac.com, BIOPAC Systems, Inc. Application Notes, Application Note 196: Cardiac output measurement—using EB/100C and LEAD110S, Sep. 25, 2008, 8 pages.

Qi et al., "correlation of a model based noninvasive measurement of cardiac output against thermodilution measurements from intensive care patients," Annual International Conference of the IEEE Engineering in Medicine and Biology Society, 1990, pp. 1040-1041, vol. 12, No. 3.

Franks et al., "Contactless respiration monitoring of infants" Medical and Biological Engineering, May 1976, pp. 306-312.

Folke, et al., "Critical review of non-invasive respiratory monitoring in medical care," Medical & Biological Engineering & Computing 2003, vol. 41 pp. 377-383.

Kwon et al., "Estimation of anomaly location and size using electrical impedance tomography" IEEE, 2003, pp. 89-96.

Bahl et al., "Microstrip loop radiators for medical applications," IEEE Transactions of microwave theory and techniques, Jul. 1982, pp. 1090-1093, vol. MIT-30, No. 7.

Hettrick, et al., "Correlation of esophageal conductance measurements wiht aortic and left ventricular diameters and stroke volume," IEEE Transactions on biomedical engineering, Apr. 2000, pp. 559-564, vol. 47, No. 4.

Camelia Gabriel, US Airforce Report ATOSR-TR-96 http://www.fcc.gov/fcc-bin/dielec_file, untitled document, accessed Jul. 13, 2009, 1 page.

Stuchly et al., "Exposure of human models in the near and far field—a comparison," IEEE Transactions on biomedical engineering, Aug. 1985, pp. 609-616, vol. BME-32, No. 8.

Gandhi et al., "Absorption of millimeter waves by human beings and its biological implications," IEEE Transactions on Microwave Theory and Techniques, Feb. 1986, pp. 228-235, vol. MIT-34, No. 2.

Iskander et al., "Electromagnetic techniques for medical diagnosis: a review," Proceedings of the IEEE, Jan. 1980, pp. 126-133, vol. 68, No. 1.

Iskander et al., "A microwave method for estimating absolute value of average lung water," Radio Science, Sep.-Oct. 1982, pp. 111S-117S, vol. 17, No. 5S.

http://butler.cc.tut.fi/~malmivuo/bem/bembook/25/25.htm, "Impedance Plethysmography" Dec. 9, 2001, 25 pages.

Iskander et al., "Microwave methods of measuring changes in lung water," Journal of Microwave power, 1983 pp. 265-275, vol. 18, No. 3.

Pedersen et al., "Microwave reflection and transmission measurements for pulmonary diagnosis and monitoring," IEEE Transactions on biomedical engineering, Jan. 1978, pp. 40-48, vol. BME-25, No. 1.

http://sbec.abe.msstate.edu/1999/abstracts/106.html, Matthews et al. "A non-contact vital signs monitor," accessed Oct. 28, 2002, 5 pages.

Johnson et al., "Nonionizing electromagnetic wave effects in biological materials and systems," Proceedings of the IEEE, Jun. 1972, pp. 692-718, vol. 60, No. 6.

Chang, John "Radar based diagnostics," date unknown, 30 pages.

Buell, James C., "A practical, cost-effective, noninvasive system for cardiac output and hemodynamic analysis," American Heart Journal, Aug. 1988, pp. 657-664. vol. 116, No. 2.

http://www.williamson-labs.com/480_hr.htm, Heart Rate, Remote Measurement, Remote heart rate and breathing rate detection, accessed Jun. 4, 2002, 7 pages.

Staal et al., "The trans-cardiac conductance method for on-line measurement of left ventricular volume: assessment of parallel conductance offset volume," IEEE Transactions on biomedical engineering, Feb. 2003, pp. 234-240, vol. 50, No. 2.

(56) References Cited

OTHER PUBLICATIONS

Peres et al., "Transmission line modeling: a circuit theory approach," Society for Industrial and Applied Mathematics, Jun. 1998, pp. 347-252, vol. 40, No. 2.

Capek et al, "Noninvasive measurement of cardiac output using partial CO2 rebreathing," IEEE Transactions on biomedical engineering, Sep. 1988, pp. 653-661, vol. 35, No. 9.

Chatterjee, "Dielectric and dielectric-loaded antennas," Research Studies Press Ltd., 1985, 7 pages.

Lu et al, "Abnormal cardiovascular response induced by localized high power microwave exposure," IEEE Transactions on biomedical engineering, May 1992, pp. 484-492, vol. 39, No. 5.

Overfelt, "Electric lines of force of an electrically small dipole-loop antenna array," IEEE Transactions on antennas and progpagation, Mar. 1998, vol. 46, No. 3.

Overfelt, "Near fields of the constant current thin circular loop antenna of arbitrary radius," IEEE Transactions on antennas and propagation, Feb. 1996, vol. 44, No. 2.

\* cited by examiner

NON-INVASIVE METHOD AND DEVICE FOR MEASURING CARDIAC OUTPUT

PRIORITY CLAIM

This application claims the benefit of U.S. Provisional Application No. 61/010,035 filed on Jan. 4, 2008 entitled "Non-Invasive Method and Device for Measuring Cardiac Output" the entirety of which is incorporated herein by reference.

GOVERNMENT

This invention was made with government support under Grant No. DAMD1700C0013 awarded by the Department of Defense. The government has certain rights in the invention.

FIELD OF THE INVENTION

The present invention relates to medical devices, and more particularly to devices and methods of operation of said devices for non-invasively measuring the cardiac output of a patient.

BACKGROUND

There are numerous parameters that are measured invasively and non-invasively to gain diagnostic information about the cardiovascular system. The major function of the cardiovascular system is to supply sufficient amounts of oxygen and nutrients to meet the metabolic demands of the tissues. Cardiac output is a primary determinant of global oxygen transport from the heart to the body and cardiovascular insufficiencies are reflected in cardiac output. Measurement of cardiac output provides both diagnostic and prognostic information, and the means to monitor the adequacy of therapy, as well as to assess the condition of a patient following a major trauma with hemorrhage and during the ensuing fluid resuscitation.

Hemorrhage is a major cause of death of battlefield casualties who are not killed immediately and survive beyond the initial five minutes from injury. Half of battlefield deaths are the result of uncontrolled bleeding. Successful treatment requires immediate medical attention that can be very limited in the battlefield until the casualty is evacuated to higher echelons of care. Monitoring of the physiological status during transport and the end points of the resuscitative treatment is critical to both immediate survival as well as long-term treatment of a patient. It has been suggested that severely injured casualties should be evacuated in less than one hour to a front-line high echelon care unit and that during initial treatment and evacuation, physiological monitoring should be used to guide resuscitation efforts.

Cardiac output is an important indicator of hemodynamic status of the circulatory system and is important in diagnosis and treatment of heart disease and in guiding fluid resuscitation following major trauma with hemorrhage. Cardiac output provides a direct measure of the heart's ability to pump blood and is determined as a product of stroke volume and heart rate. As the hemorrhage progresses, arterial blood pressure decreases and sympathetic compensatory mechanisms are activated that shunt the blood from the peripheral to central compartment in order to maintain blood pressure and thus oxygenation of vital organs. In healthy and physically trained individuals, these compensatory mechanisms maintain blood pressure disproportionately high within the body only to cause a rapid circulatory collapse as the hemorrhage causes massive loss of blood volume. Cardiac output, in turn, reacts faster to the progression of hemorrhagic shock and drops sooner than the arterial pressure in response to blood loss during hemorrhage. Early intervention and resuscitation based on monitoring of cardiac output is the most complete way of capturing the physiological impact of the hemorrhage and resulting circulatory shock. In addition to the delay in blood pressure drop caused by the compensatory mechanisms, arterial blood pressure is not available under battlefield conditions and is commonly substituted by traditional, non-invasive (occlusive) blood pressure measurements in peripheral circulation. As mentioned above, the compensatory mechanisms that maintain blood supply to the vital organs do so by increasing peripheral resistance and diverting blood from the peripheral to central pool, causing the cessation of pressure pulse in peripheral circulation, and further difficulties in the determination of blood pressure. Although blood pressure is currently used to monitor the progression of hemorrhagic shock and the effectiveness of fluid resuscitation, direct measurement of cardiac output would provide a more effective, direct measure of both and, consequently, a more effective therapy.

Clinicians have an increasing number of available sensors and instrumentation that support measurements of cardiac output. These include, without limitation, indicator dilution techniques with or without the use of a pulmonary artery catheter, arterial pulse contour techniques, aortic pulsed Doppler, both of the ascending and descending aortas, indirect measures using arterio-venous gas content differences and expired gas measures via the Fick's equation, and bio-impedance techniques. Due to the high costs and need for highly specialized medical personnel and well-equipped facilities, as well as potentially severe complications associated with invasive measurement of cardiac output, noninvasive techniques are highly desirable. For battlefield applications, only non-invasive methods that require minimal skills and that can be deployed under "far forward" and "casualty transport" conditions are practical. None of the above methods has as yet fulfilled these requirements.

SUMMARY OF THE INVENTION

In light of the problems and deficiencies inherent in the prior art, the present invention seeks to overcome these by providing a method of measuring cardiac output of a person, the method comprising placing a device about the mid-sternal position on the person, said device comprising a RF signal generator coupled to an antenna, said antenna having a dielectric material disposed about the exterior of the antenna. The method further comprises propagating a first signal having a predetermined frequency towards the heart of the person and receiving and measuring a portion of the first signal returned from the heart of the person with the device. The method further comprises comparing the magnitude of the first signal propagated into the heart of the person to the magnitude of the portion of the first signal returned from the heart of the person and calculating a return loss of the signal. Additionally, the method comprises propagating an additional signal into a portion of the heart of the person using the device, wherein said additional signal has a frequency different from the first signal and receiving and measuring a portion of the additional signal returned from the heart of the person with the device. The method further comprises comparing the magnitude of the additional signal propagated into the heart to the person to the magnitude of the additional signal returned from the heart of the person and calculating a return loss of the additional signal as well as comparing the return loss of the first signal to the return loss of the additional signal. The method further comprises repeating certain steps referenced above while incrementally varying the frequency of the signal with each repetitive step and determining a maximum return loss value of the signals propagated into the heart.

In accordance with additional embodiments, the present invention improves upon deficiencies in the prior art by providing a system for measuring the cardiac output of the heart of a patient, comprising a hand-held device comprising a housing containing a signal generator coupled to an antenna and a dielectric material disposed about the antenna, wherein said hand-held device is adapted to generate a plurality of radio frequency signals and direct said signals towards the heart of the person and measure a magnitude of a signal returned from the heart of the person. The hand-held device further comprises a processor contained within said housing, wherein said processor is adapted to compare differences between a magnitude of a signal propagated into the heart of the person and the magnitude of the signal returned off the heart. The processor is further adapted to determine a signal frequency having a maximum return loss value based on the differences between the magnitude of the signal propagated into the heart of the person and the magnitude of the signal returned off of the heart of the person. Additionally, the processor is further adapted to estimate a change in the amplitude of motion of a portion of a wall of the heart based on the differences between the magnitude of the signal propagated by the device and the magnitude of the signal returned off of the portion of the heart.

BRIEF DESCRIPTION OF THE DRAWINGS

The present invention will become more fully apparent from the following description and appended claims, taken in conjunction with the accompanying drawings. Understanding that these drawings merely depict exemplary embodiments of the present invention they are, therefore, not to be considered limiting of its scope. It will be readily appreciated that the components of the present invention, as generally described and illustrated in the figures herein, could be arranged and designed in a wide variety of different configurations. Nonetheless, the invention will be described and explained with additional specificity and detail through the use of the accompanying drawings in which:

DESCRIPTION OF EXAMPLE EMBODIMENT(S)

The following detailed description of exemplary embodiments of the invention makes reference to the accompanying drawings, which form a part hereof and in which are shown, by way of illustration, exemplary embodiments in which the invention may be practiced. While these exemplary embodiments are described in sufficient detail to enable those skilled in the art to practice the invention, it should be understood that other embodiments may be realized and that various changes to the invention may be made without departing from the spirit and scope of the present invention. Thus, the following more detailed description of the embodiments of the present invention is not intended to limit the scope of the invention, as claimed, but is presented for purposes of illustration only to describe the features and characteristics of the present invention, and to sufficiently enable one skilled in the art to practice the invention. Accordingly, the scope of the present invention is to be defined solely by the appended claims.

The following detailed description and exemplary embodiments of the invention will be best understood by reference to the accompanying drawings, wherein the elements and features of the invention are designated by numerals throughout.

In accordance with one embodiment of the invention, a method and device are disclosed for measuring the cardiac output of a patient. The method and device are based on the general operating principle that alternating current electrical signals used to produce and detect radio waves may be utilized to detect the status of biological systems within the body. Generally speaking, radio waves are propagated into the body. A certain portion of those waves are absorbed by the body. A certain portion of the waves not absorbed by the body are returned back near their point of origin. The difference between the magnitude of the waves sent into the body and the magnitude of the waves returned back near their point of origin (referred to herein as "return loss") is utilized to estimate certain characteristics of biological tissue (e.g., cardiac tissues) within the body. Additional details regarding the signal propagating device and method of estimating cardiac output from data the device gathers are presented in turn below.

The present invention provides several significant advantages over prior related medical device. Many advantages will be apparent in light of the detailed description set forth below, with reference to the accompanying drawings. These advantages are not meant to be limiting in any way. Indeed, one skilled in the art will appreciate that other advantages may be realized, other than those specifically recited herein, upon practicing the present invention.

RF Device

Figure 1:
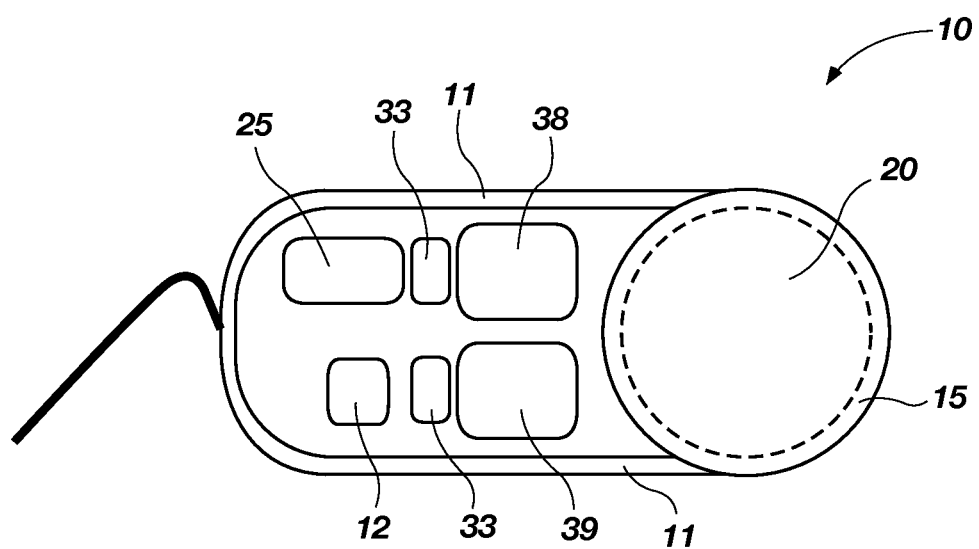
FIG. 1 shows one embodiment of an RF device in accordance with one embodiment of the present invention.
Figure 2:
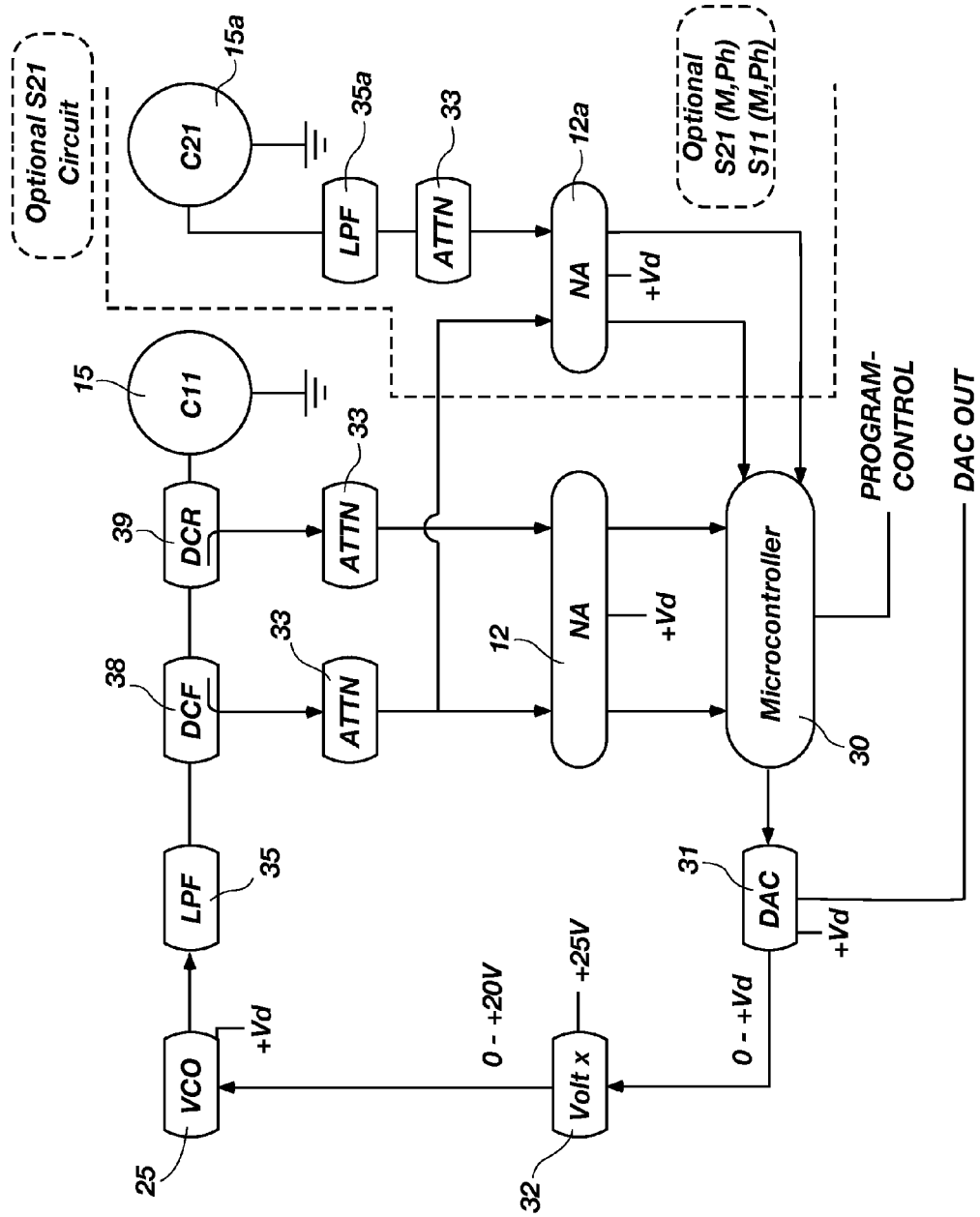
FIG. 2 shows a schematic block diagram of a RF device in accordance with one embodiment of the present invention.
Figure 3:
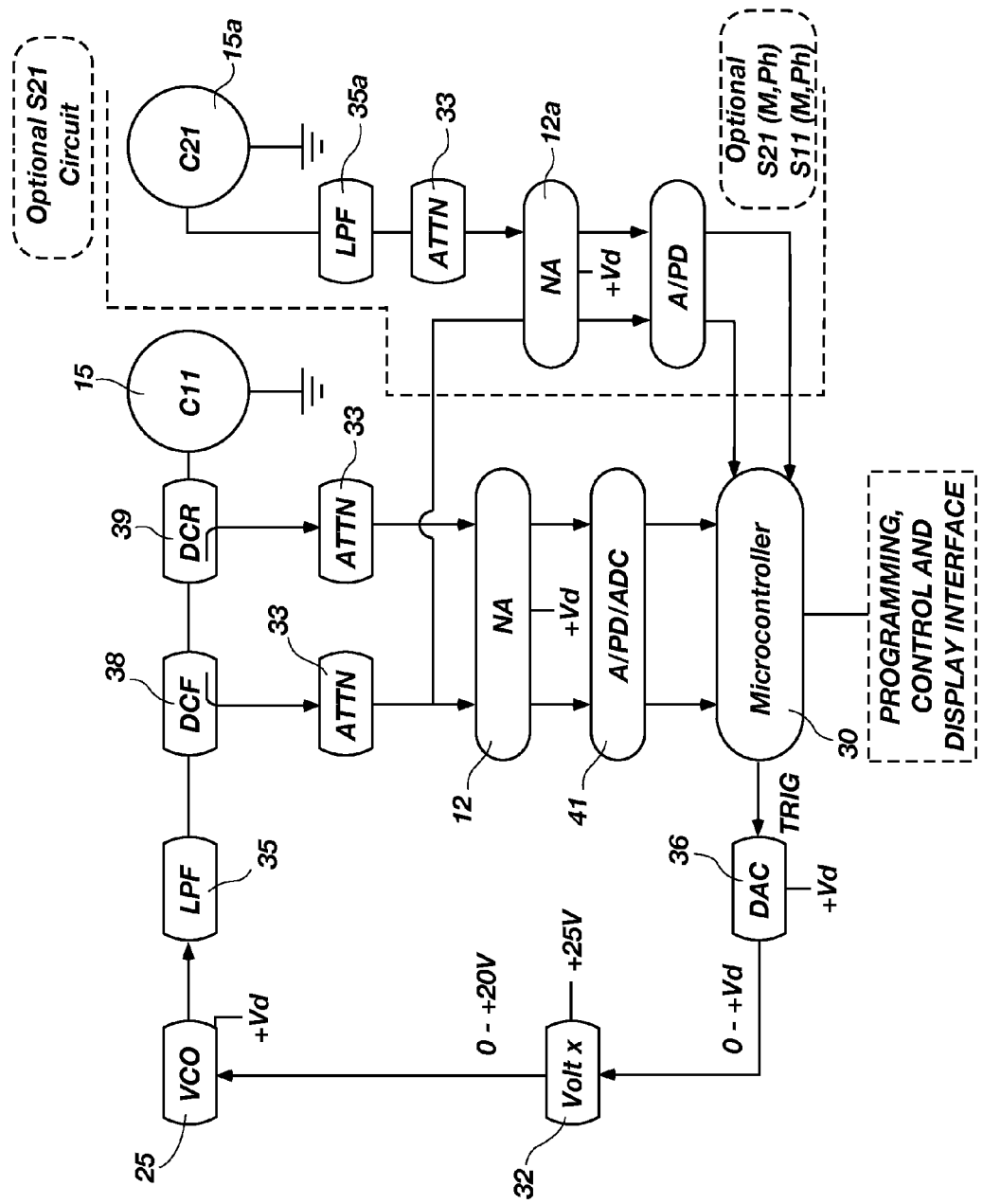
FIG. 3 shows a schematic block diagram of a RF system in accordance with one embodiment of the present invention.

With reference now to FIGS. 1 through 3, and in accordance with one embodiment of the invention, a device 10 for estimating changes in the cardiac output of a patient is disclosed comprising a radio frequency ("RF") signal generator coupled to an antenna 15, said antenna 15 having a dielectric material 20 disposed about an exterior surface of the antenna 15. The dielectric material 20 may be disposed about select portions of the exterior surface of the antenna 15 or substantially about the entire exterior surface of the antenna 15.

The RF signal has a near field component and a far field component. In one aspect of the invention, the dielectric material 20 has a predetermined thickness and a predetermined dielectric constant such that a substantial portion of the near field component of the electronic signal returned from the patient is not received by the antenna 15. In one aspect of the invention, the dielectric material 20 is designed such that substantially the entire near field component of the electronic signal returned from the patient is not received by the antenna 15. In one embodiment, the dielectric material 20 has a dielectric constant ranging from 5 to 25 and has a thickness ranging from 2 mm to 20 mm. Importantly, the design of the dielectric material 20 is dependant upon numerous characteristics which vary depending on the type of dielectric material used. That is, the thickness of the material is a function of its dielectric constant and thus it is specific for a given material. Accordingly, no limitation should be read into the exact specifications of the dielectric material used herein.

With reference to FIG. 2, a block diagram of the RF device with digital detection means in accordance with one embodiment of the present invention is illustrated. In one aspect of the invention, the RF signal is generated by a voltage controlled oscillator 25 ("VCO") contained within a device housing 11. The VCO 25 generates the RF signal at differing frequencies by varying the tuning voltage. Examples of VCO's 25 which may be used include the ROS-2150 made by Minicircuits, however any VCO 25 capable of generating an appropriate RF signal may be utilized. As noted herein in more detail, initially, a micro-controller 30 via a digital to analog ("D/A") converter 31 sweeps the frequency of the RF signal between approximately 1000 and 2000 MHz by causing the tuning voltage to vary between approximately zero and 20 volts. In one aspect of the invention, the output of the VCO 25 is less than 4 mW. While any suitable operating frequency may be used, in one embodiment of the present invention, the VCO 25 operates at a frequency ranging from 0.5 GHz to 2.5 GHz.

In one aspect of the invention, the device 10 further comprises a network analyzer 12 such as that manufactured by Analog Devices (AD8302IC). The detector is capable of identifying the magnitude and phase of subject signals and has a 60 dB dynamic range and outputs a magnitude voltage of 30 mV per dB of return loss. The phase output is 10 mV per degree over 180 degrees. The device 10 further comprises microcontroller 30 (such as those manufactured by Cygnal) to read the network analyzer outputs, determine the minimum or maximum values of magnitude and phase during a frequency sweep and generate a digital sweep that enters the D/A converter 31 that then drives the VCO 25. This closed loop generates the VCO sweep, determines the frequency of maximum return loss (magnitude or phase), and then locks on to that frequency. As the heart beats or lungs move, the microcontroller 30 tracks the magnitude and phase of the "organ's" signal.

In one aspect of the invention, a low pass filter 35 ("LPF") is used to prevent the VCO second harmonic from entering the network analyzer 12 (e.g., AD8302 magnitude and phase integrated circuit). In one aspect, the LPF 35 has a −3 dB "corner" frequency of 1700 MHz. In an additional aspect of the invention, the LPF output is routed to two directional couplers 38. The directional couplers 38, 39 sample the RF signal both in the forward (38) and reverse (39) directions. In one embodiment, the sampled signal is 20 dB down from the transmitted signal. In an additional aspect, directional couplers 38, 39 exhibit directivity. That is, they are relatively insensitive to signals coming in a reverse direction. The directional couplers 38, 39 noted herein have directivities of 20 to 34 dB depending on the frequency of the RF signal. The transmitted RF energy goes to the antenna 15 where the coupled signals are routed to the network analyzer 12. A voltage multiplier 32 and appropriately placed attenuators 33 may also be used in accordance with certain aspects of the invention. In one aspect, appropriate programming control and display interfaces are incorporated on the face of the RF device. In other aspects, the programming control and display interfaces are located on a remote programming device.

With reference now to FIG. 3, a block diagram of the RF device with analog detection means in accordance with one embodiment of the present invention is illustrated. While similar to the digital detection system shown in FIG. 2, additional components are shown to achieve proper detection of an analog signal. Additional components include a sawtooth generator 36, a generator trigger signal 37 and an amplifier/signal conditioner/peak detector/analog digital converter device 41.

Referring generally again to FIGS. 1 through 3, the RF components discussed herein are fitted to a 4 layer PCB with 50-ohm traces. The RF board components are shielded and, in some embodiments, feed through capacitors are used to prevent RF signals from "leaking out" of the shield via the DC or low frequency signals. In accordance with one aspect of the invention, the device is capable of measuring the signal transmitted from the VCO 25 to an antenna 15 where the signal has been modulated by the organ system of the patient. In this aspect, the device 10 comprises an additional dipole antenna 15*a*, an additional LPF 35*a*, a single directional coupler and a second network analyzer 12*a*, one of whose inputs is from the VCO 25. Output from the network analyzer 12*a* is routed to the data collection system.

In one embodiment of the present invention, the device further comprises a switch sensor for activating and deactivating the device 10. The switch sensor would activate the device 10 only when it is in full contact with the body of the patient and would deactivate the device 10 when not in full contact with the body. Advantageously, errant RF radiation emitted into the surrounding environment would be minimized by using the switch sensor. The switch sensor may comprise a touch-activated switch sensor or other desirable switch sensor as suits a particular application.

Coupling of the RF signal into the body is maximized when there is a good impedance match between the coupler and the body. It is believed that biological tissues present about a 50-ohm load for the RF signal. Appropriately placed dipoles and loop antennas provide as much as 50 dB return loss at frequencies when placed near the body, even through clothing. As the antenna 15 nears the body, the tissue loads the antenna 15 changing its resonance to below that of free-space resonance. In accordance with one aspect of the invention, the measurement of the return loss is performed at 1 millisecond intervals, resulting in 1 kilosample per second signal acquisition rate. As noted above, the core of the system is the network analyzer 12 which measures the ratio of the returned RF signal to the sampled outgoing signal generated by the VCO 25. The optimal frequency of the VCO 25 is found by scanning the frequency range within approximately 1-2 GHz range and determining the frequency of the maximum return loss. The magnitude, phase, and frequency at the maximum return loss point is then digitized and displayed and/or stored in the data file. Additional functions of the device included acquisition of up to 4 analog channels (e.g., flow, impedance, ECG, other) of 0-5V range and synchronizing the analog data channels with the RF magnitude, phase and frequency.

In accordance with one aspect of the invention, a dipole antenna is utilized which comprises copper foil tape applied to a suitable backing substrate. A 50-ohm coaxial cable connects the dipole antenna to a processor.

In accordance with an additional embodiment of the present invention, a full wave loop antenna placed in a cylindrical shield may be utilized. As is the case with many biomedical sensors, the output of the sensor (i.e., the antenna) is affected by multiple factors giving rise to common mode error, such as sensor-body interface, relative motion of the sensor and the tissues at the sensor placement site, RF absorption and reflection by internal body organs other than the heart, and by motion artifacts generated by both intrinsic (e.g., breathing) and external factors (e.g., sensor pressure, sensor motion, etc.). Interfacial motion generates signal components that are much larger than the signals related to the heart and therefore it is essential to provide signal conditioning and data processing that can separate the signal of interest. That is, signals that relate to the stroke volume of the heart need to be measured while also preserving the breathing and respiratory components of the measured signal, such as breathing rate and depth. The difficulty of achieving these tasks is compounded by small levels of the RF signal from the sensor and the resulting low Signal to Noise ratio (SNR), and by the high ratio of the DC to AC component of the return loss signal.

Generally speaking, interactions of electromagnetic fields with matter are a function of frequency, dielectric, conductive and magnetic properties of the material, geometry of the radiating element (antenna) and distance, and orientation of the antenna with respect to the observation point. Calculations of an antenna field have been extensively studied for different antenna configurations, sizes and materials, and fundamental equations approximating electric and magnetic fields for simple antenna geometries and homogeneous media, are available. However, in cases of either complex antenna shapes or non-homogeneous media, calculations are very difficult, if possible. Therefore, while the following analysis is an oversimplification of the actual setting, it provides significant insights into the origin of motion artifact and offers a practical way of reducing the influence of undesirable interference. In one aspect of the present invention, a circular loop antenna was employed for which the components of the electric and magnetic field as a function of distance from the antenna are given by numerous equations. These equations represent fields resulting from a sinusoidally-excited current loop with a magnetic moment "dm". Electric and magnetic components of the field are given by the relationships:

$$E\phi_i = 30\beta^3 * dm * [1/(\beta r) - j/(\beta r)2] \sin(\theta) * e(-j(\beta r))$$

The electric field contains components are proportional to the $1/(\beta r)$ and $1/(\beta r)2$ and magnetic field components which are a function of $1/(\beta r)3$ where r is a distance from the radiating element, and ($\beta$ is a wave number, ($\beta=2Pi/\lambda$). Therefore, the behavior of the complex electric field as a function of distance is determined by the functions: $1/(\beta r)$, and $1/(\beta r)2$, $1/(\beta r)3$ for magnetic components)

Figure 4:
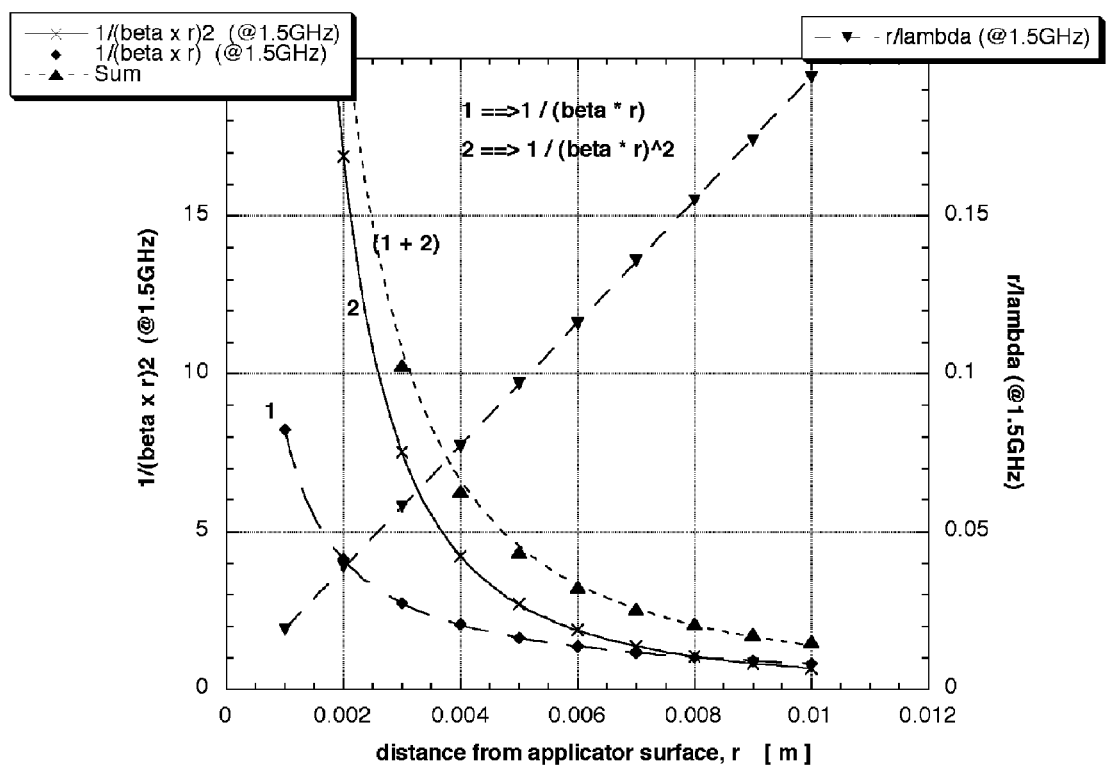
FIG. 4 illustrates calculated contributions to a complex electric field of certain terms in a near field region of a circular loop antenna in a material with a relative dielectric constant in accordance with one embodiment of the present invention.

If the boundary between near and far electrical field is defined as a distance at which $r/\lambda=\frac{1}{2}Pi$, then at that distance the contributions of each of the terms $1/(\beta r)n$ becomes equal (i.e., for $r=\lambda/2Pi$, $1/(\beta r)\approx1/(\beta r)^2$). In the near field, the higher power term, $1/(\beta r)^2$ dominates the complex field components, while beyond that limit, the contribution of this term becomes insignificant and the electric field is determined by a familiar relationship: $E\approx1/r$. Thus, it is believed that any interactions between the radiated EM wave and an object will be stronger in the near field region than in the far field. FIG. 4 illustrates the calculated contributions to the complex electric field, of the $1/(\beta r)n$ terms (curves 1, 2) in the near field region of the circular loop antenna in the material with the relative dielectric constant $\in r=15$. In the material with such high dielectric constant, the wavelength, 1, at 1.5 GHz is only about 5 cm ($\lambda=c/f*(1/sqrt(\in r))$), where c is the speed of light and f is the frequency. Curve (1+2) represents the sum contribution from the $1/(\beta r)^n$ components.

The above analysis suggests that at the frequency range of interest all the interactions between the antenna and the body surface of the patient occur within the near-field distance, and therefore tend to be dominated by higher-power terms of the complex field, while the impact of the heart (that is positioned under the tissues in the distance of more than 2 cm from the surface) is dominated by the $1/(\beta r)$ term, which varies much slower than the quadratic term. Accordingly, it is believed that a circular loop antenna would be expected to exhibit much higher sensitivity to interfacial motion than to the motion/absorption at the tissues and organs at distances further away from the antenna surface, especially considering that the wavelength inside the body is even shorter (average dielectric constant of the tissues is about 50, therefore $\lambda\approx2.4$ cm).

Accordingly, it is believed that if the near-field region is contained within the stationary (not subject to interfacial perturbations) antenna limit, and all the interactions between the antenna and the body could be limited to the far-field region where the complex field is dominated by the 1/r term only, the return loss sensitivity would be the same for all the interactions contributing to the return loss signal of the sensor. That is, the relative contribution from the surface motion artifact to the signal would be greatly reduced. As such, by disposing a dielectric material about the antenna, motion artifacts are greatly reduced.

Figure 5:
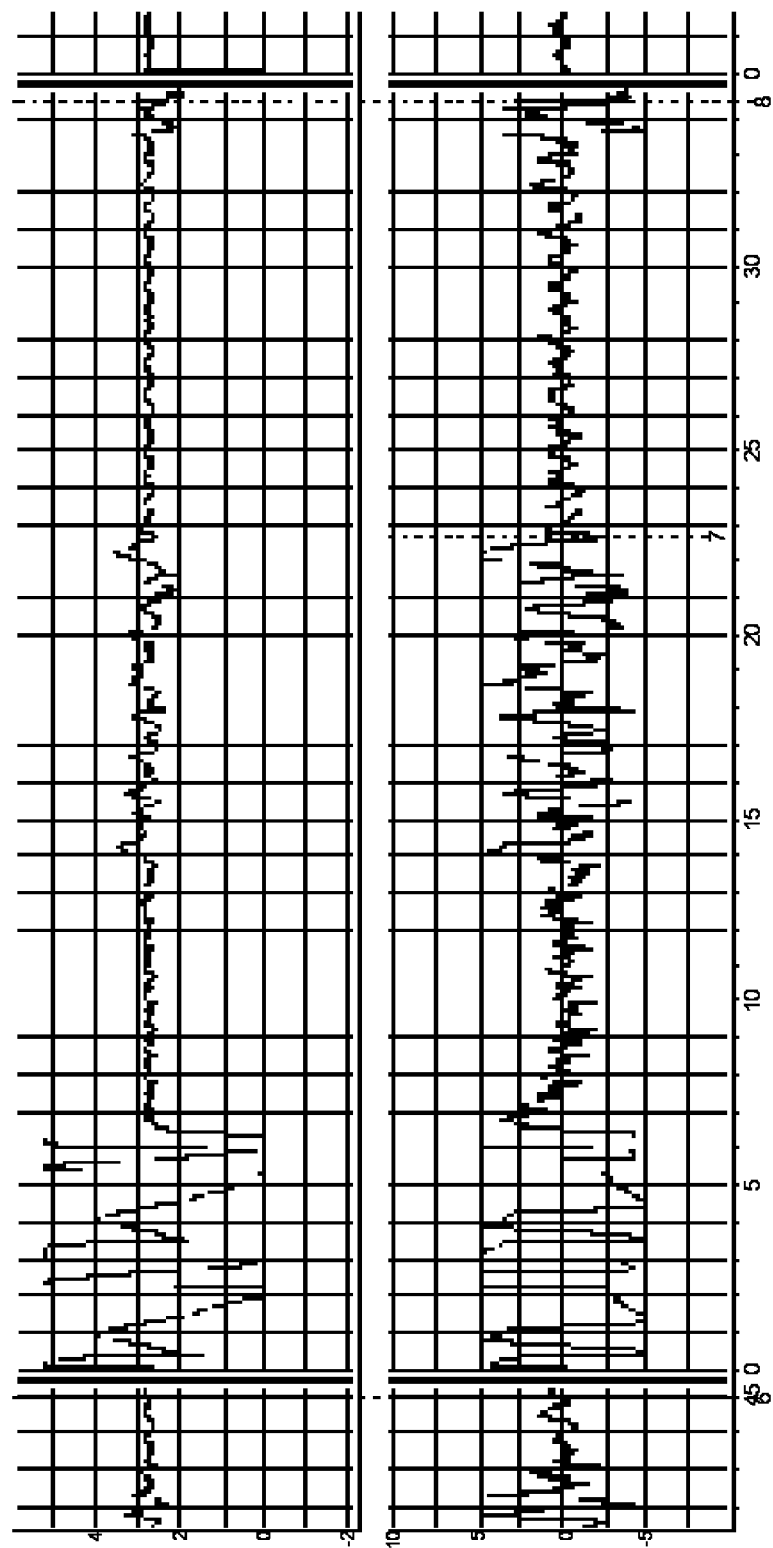
FIG. 5 shows a comparison of the sensor signal with and without motion artifact reduction in accordance with one embodiment of the present invention.

In one embodiment of the present invention, ceramic disks of 8.5 mm and 5.5 mm thickness and $\in r=15$ are attached to the front surface of the antenna 15. The results of tests of monitoring of the heart and breathing action in human volunteers in the presence and absence of the interfacial motion are shown in FIG. 5. Advantageously, the output signal of the antenna 15 having the dielectric material 20 was attenuated as compared to the signal measured with the antenna 15 without the dielectric material 20. However, the signal was much less sensitive to motion artifacts induced by moving the antenna 15 with respect to the surface of the patient. While the bandwidth of the signal detected by the device 10 after passing through the dielectric material 20 is reduced, thereby making the system less efficient, without the dielectric material 20, the motion artifact signal entirely obliterates the heart beat signal.

For the frequencies used in the testing of the device 10 (e.g., 1000 MHz to 2000 MHz), the motion artifact-related signal originated in the near-field of the antenna 15 (i.e., at the interface between the antenna and the body). In this region, complex electric field modulation is dominated by fast changing $1/r^2$ function, whereas in the far field, these interactions result in a slower 1/r relationship. Placing a dielectric material 20 on the surface of the antenna 15 causes shortening of the wavelength in the dielectric region by a factor of $1/(sqrt(\in r))$. Thus, a proper selection of the dielectric material 20 and its geometry (thickness), permits enclosing the near-field region entirely in the dielectric material, resulting in the significant reduction of the device sensitivity to interfacial motion as noted above.

While specific reference has been made herein to ceramic as a dielectric material 20, any desirable dielectric material may be utilized as suits a particular application. Example dielectric materials include ceramics, glass, plastics, and polymers. Fluid dielectric materials may also be used as desired including, but not limited to gels, liquids, polymeric fluids, and hydrocarbon-based fluids. Additionally, while specific reference has been made to a specific thickness, it is important to note that the thickness of the dielectric material 20 will vary according to the type of dielectric material used.

In an additional embodiment of the present invention, additional modifications to the antenna 15 were made to minimize motion artifact. As has been discussed herein, the antenna 15 is very sensitive to tangential (lateral), as well as normal motion of the antenna 15 with reference to the skin surface. The sensitivity includes changes in the force of the sensor on a surface of the body. These factors affected both the initial sensor coupling to the body (DC loading level, dB), and to the lesser extent, an AC component of the signal.

As noted above and in accordance with one embodiment of the present invention, a pressure sensor is coupled to the device 10 to detect the application force and motion of the antenna 15 with reference to the body. Sensor software can be created to permit valid data measurements only while the sensor is balanced and indicates "no-motion" conditions. In one aspect of the invention, pressure sensors are disposed on all four corners of the antenna 15 and are connected to a quad bridge circuit. In one embodiment of the antenna design, three strain gages are built into the applicator shield and used in the same manner. Software is programmed into the network analyzer 12 to visually show the strain on each gage and prevent measurement if the difference in strain exceeds an adjustable threshold. An indicator light is disposed on the device 10 so the user knows when the strain is equal on all three gages thus indicating the applicator is evenly positioned.

Figure 6:
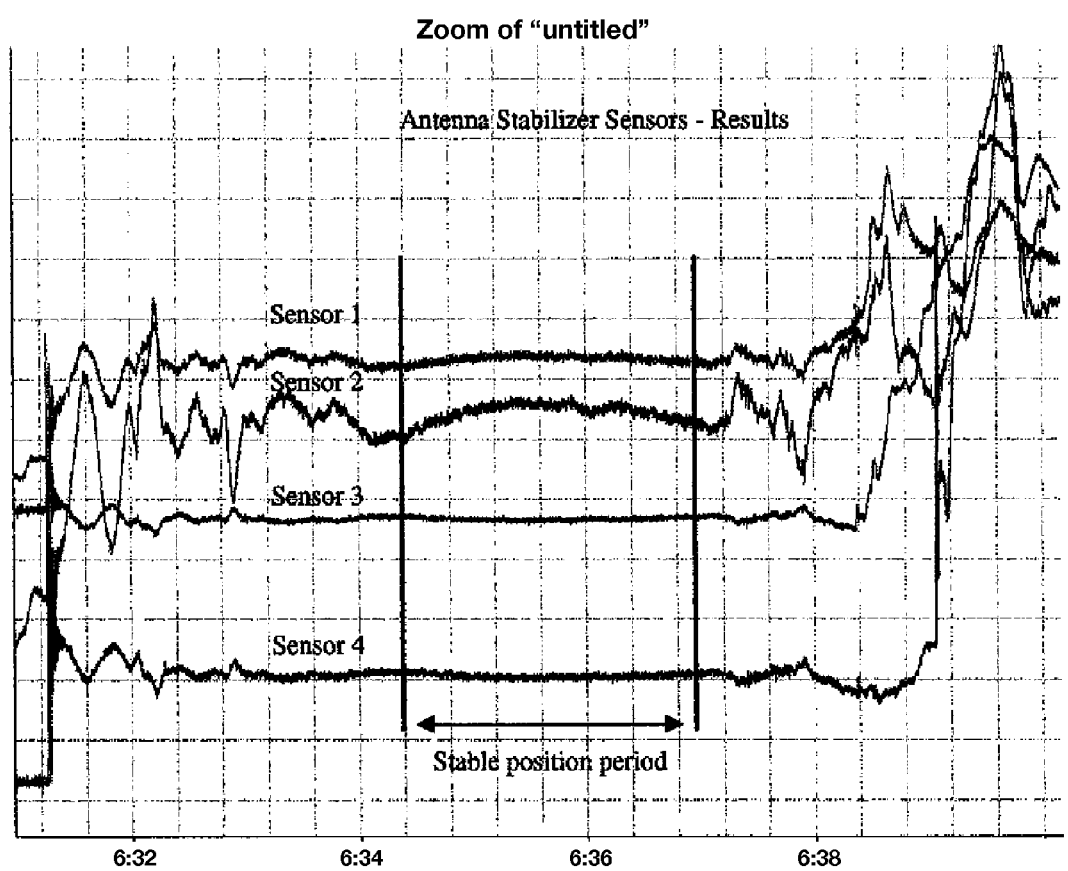
FIG. 6 shows a record of pressure sensor stabilizer data in accordance with one embodiment of the present invention.

An example force sensor-based stabilization signal is shown in FIG. 6. At the left of the graph, the sensor applicator is pressed against the chest and the variation in the sensor signal is illustrated. Towards the center of the graph, applicator motion becomes minimal and the sensor is stabilized. On the right hand side of the graph, sensor motion is again occurring and as such, data should not be recorded. Illustrated further in FIG. 5, are example sensor signals with and without motion artifact reduction. The signal at the left of the top panel graph is off-scale and cannot be interpreted while suppressing the motion-free signal segment. The bottom panel illustrates the result of sensor signal measurement with motion artifact reduction design.

Signal Processing and Non-Invasive Method of Measuring Cardiac Output

In accordance with one embodiment of the present invention and as described in more detail through this application, a method for estimating certain parameters of a person's cardiac output is disclosed. Broadly speaking, the method comprises placing a device 10, such as that described in the preceding sections of this application, about the mid-sternal position of the person. The device 10 comprises an RF signal generator 25 coupled to an antenna 15, said antenna 15 having a dielectric material 20 disposed about the exterior 16 of the antenna 15. The method further comprises propagating a first signal having a predetermined frequency towards the heart of the person and receiving and measuring a portion of the first signal returned from the heart of the person with the device 10. The magnitude of the first signal propagated into the heart of the person is compared to the magnitude of the portion of the first signal returned from the heart of the person and a return loss of the signal is calculated. The method further comprises propagating an additional signal into a portion of the heart of the person using the device, wherein said additional signal has a frequency different from the first signal and receiving and measuring a portion of the additional signal returned from the heart of the person with the device 10. The magnitude of the additional signal propagated into the heart to the person is then compared to the magnitude of the additional signal returned from the heart of the person and a return loss of the additional signal is calculated. The method further comprises comparing the return loss of the first signal to the return loss of the additional signal and repeating certain of the above-referenced steps while incrementally varying the frequency of the signal with each repetitive step. The method also comprises determining a maximum return loss value of the signals propagated into the heart of the person over the utilized frequency range. As noted above, in one embodiment, the frequency of the signal is swept between 1000 and 2000 MHz in an effort to determined the maximum return loss for a particular patient at a particular frequency.

It is believed that proper positioning of the device 10 on the patient is important for optimal operation of the device. In one aspect of the invention, optimal results are obtained when the device 10 is positioned in the mid-sternal position. That is, the optimal results are obtained when the signals from the device are predominantly focused on the right ventricle of the patient's heart.

In an effort to understand the physiological interpretation of the RF device signal, a time-domain analysis of the RF signal was recorded synchronously with a 3-lead ECG (RA-LA-LL). A comparison of that analysis is explained in more detail below and illustrated in the attached figures. Generally speaking, the cardiac cycle consists of two major periods, systole, during which the ventricles contract and, under high pressure, eject blood into the pulmonary artery and into the aorta, and diastole, during which the heart is in its low pressure state and the ventricles are filling with blood. At the beginning of the systole, the heart is maximally extended, while at the beginning of the diastole the extension of the heart muscle is minimal. The systole starts with the R-wave, which is immediately followed by contraction of the left ventricle, and ends after the T-wave with the closing of the aortic valve. According to Frank-Starling Law of the heart, tension developed in cardiac muscle fibers is proportional to their stretching and thinning, or to the volume of blood filling the heart, or End Diastolic Volume ("EDV"). The EDV is one of the factors that determine the size of the subsequent stroke volume. If a signal is proportional to the volume of the right ventricle, the magnitude of the signal should vary between cardiac cycles with the venous return, or preload. Therefore, the device acts as a sensitive indicator of the physiological events that affect venous return.

Immediately following the R-wave, both tricuspid and pulmonic valves are closed, and the initial ventricular contraction results in an isovolumetric intraventricular pressure build-up. With general reference now to FIG. 7, based on the comparison of the left ventricular pressure wave and S-wave timing, components of a recorded RF signal can be identified that correspond to mechanical contraction of the heart and thus provide information about changes in the cardiac output. In one aspect of the invention, an analysis begins with the R-wave, which initiates contraction of the ventricles. Upon contraction, with some delay related to spreading of the electrical wave, the ventricles contract isovolumetrically (both valves are still closed). During isovolumetric contraction, the RS trade rises initially slowly, then rapidly, indicating a thickness change of the ventricular wall as detected by the antenna, consistent with contraction of the left ventricle. When the LVP exceeds the End Diastolic Pressure ("EDP") in the aorta, the aortic valve opens and blood is ejected from the left ventricle into the aorta, initially rapidly, and then slowly as the aortic pressure rises to the End Systolic Level, resulting in reduced low. During this period, the left ventricle reaches its minimum volume (maximum point on the RS curve), and starts expanding. Also during this period, the RS reaches its maximum. That is, the heart wall has reached its maximum thickness. As the LVP declines, the aortic valve closes. The left ventricle continues to relax, with both valves closed (isovolumic relaxation), resulting in reduced thickness of the ventricular wall, which appears on the RS as a section with significantly reduced slope. As the ventricular pressure drops below the level of atrial pressure, the mitral valve opens, initiating the period of rapid filling. The ventricular wall continues thinning as blood fills the ventricle. Both mitral and aortic valves are closed, and the left ventricle continues its (isovolumic) relaxation. When the LVP drops below the atrial pressure, the mitral valve opens, and the ventricle fills with blood, expanding its size and causing a thinning of the wall. The minimum of the RS curve corresponds to a filled ventricle ready for ejection following atrial contraction (P-wave). Following the P-wave, the mitral valve closes, and the cycle begins again. Similar pressure-valve opening/closing relationships are also true for the right atrium, right ventricle closing and opening of the pulmonic valve during systole.

Figure 7:
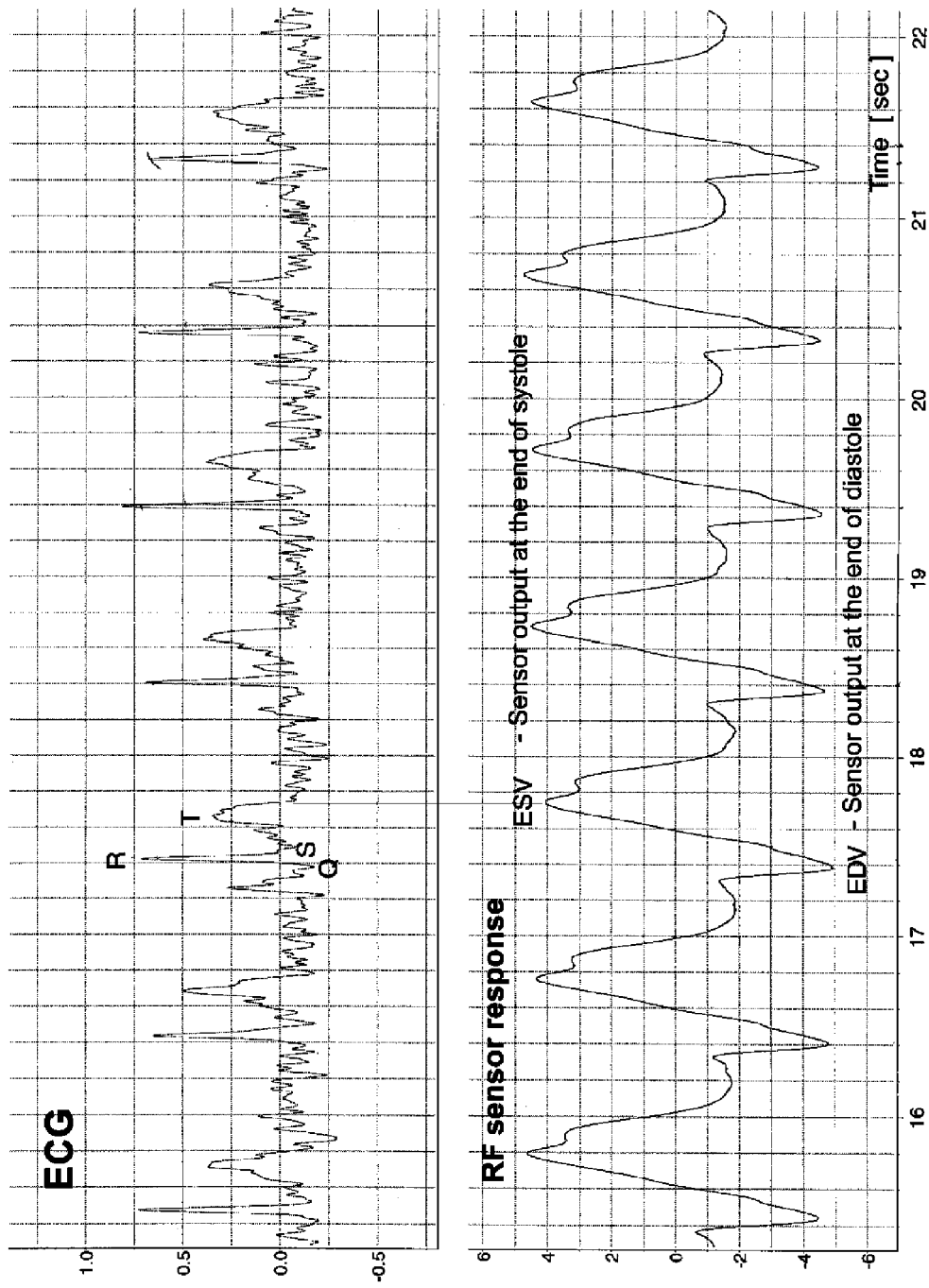
FIG. 7 shows a comparison of an ECG trace synchronously recorded with signals using an RF system in accordance with one embodiment of the present invention.

Based on this relationship between data points shown in FIG. 7, it is believed that (i) the positive slope indicates increasing return loss (less return of the RF signal), (ii) the section curve corresponding to isovolumic relaxation is either more ($1^{st}$ trace) or less (last trace) pronounced, as the filling of the heart is influenced by the intrathoracic pressure during the breaching cycle, (iii) the negative slope of the return loss curve indicates decreasing return loss, (iv) the section of the Recorded Signal trace corresponding to the filling cycle is flat due to atrial "pull," and (v) the top section of the left intraventricular pressure curve is flat due to saturation of the LVP sensor. As a result, the correlation of return loss signal and movement of the ventricular wall enables estimation of the magnitude of movement of the heart wall and thereafter information regarding changes in stroke volume and cardiac output.

Signal Modeling

According to one embodiment of the present invention, the device described in detail above utilizes the interaction of electromagnetic energy with biological tissues. The RF device utilizes the interaction of electromagnetic energy with biological tissues. Generally speaking, biological tissues are characterized by their conductivity and dielectric constant. It is believed that the magnetic permeability (μ) of tissues is similar to that of free space, and thus it is assumed that μ=1. These properties are a function of frequency and tissue type. The FCC has compiled a database of these properties at http://www.fcc.gov/fcc-bin/dielec.sh and this database was used extensively throughout the research and development of the RF device described herein.

The interaction of electromagnetic ("EM") energy with materials can be described by several important equations. The equation $\lambda=\alpha+j\beta$ where gamma is the complex propagation constant, alpha is the attenuation constant and beta is the phase constant is helpful for understanding modeling of the device signals. It is important to note that these "constants" are constant for only one frequency and particular material. That is, as the signal frequency is varied and the subject tissue is changed, the constants are variable. Beta is equal to 2*pi/lambda, the wavelength in the material. Alpha has the units of Nepers/meter. For lossy dielectrics the propagation constant can be written as $$\lambda = j\omega\sqrt{(\mu\in)} * \sqrt{(1-j(\sigma/\omega\in)}$$

where omega is the radian frequency, μ is the permeability of free space, epsilon is the permittivity of the material and sigma is the material's conductivity (Siemens/meter). The intrinsic impedance of a lossy dielectric is given by:

$$\eta = \sqrt{((j\omega\mu)/(\sigma+j\omega\in))}$$

EM energy is attenuated by lossy dielectrics and returned at impedance boundaries. A useful equation is the transmission line equation that describes the impedance seen by an EM wave as it traverses materials of differing impedance. Thus the impedance looking into a series of slabs of material is:

$$\eta_{in} = \eta_1(\eta_2 + j\eta_1 * \tan \beta 1)/(\eta_1 + j\eta_2 * \tan \beta 1))$$

where 1 is the thickness of material 1.

To estimate the amount of the signal returned from the muscle/blood interface, the intrinsic impedances of muscle and blood are estimated to be: muscle (49.2+j5.91) and blood (46.5+j7.69) (note that the real part of the impedances is very close to 50 ohms so the tissues present a good match to 50 ohm cable). To estimate the amount of energy that is returned from the blood/muscle interface it is assumed that $\rho=(Z_1-Z_0)/(Z_1+Z_0)$ where $Z_1$ and $Z_0$ are the complex impedances of the load (blood) and line (muscle). Thus $\rho=(-0.0247, \angle 0.022)$ and about 2.5% of the energy is reflected at the muscle blood interface. There is also a change in the phase of the returned wave referenced to the incoming wave of 0.022 radians. These background assumptions allow for the construction of more complex models where there are multiple slabs including air layers representing different tissue layers, such as heart wall, heart ventricle, etc.

Of the possible approaches to examine the coupling of RF EM energy into the body, two are discussed below. First, the body is a load presented to a transmission line via an "antenna coupling device" or second, an EM wave impinges on the body in the antenna's near field. Such an approach is an oversimplification but provides a qualitative assessment of the interaction of the applicator with the body.

One objective of developing a simplified propagation model for calculating RF properties of the antenna as a function of cardiac output and presence/absence of hemo/pneumothorax was to determine whether, given the dielectric properties of the tissues at the frequency range between 1 and 2 GHz, using a simplified 2-D slab configuration.

The model is based on the interaction of a planar electromagnetic wave with the body tissues modeled as slabs and has not been designed to provide predictive information, but to assist in understanding the behavior of the reflection coefficient as a function of the changes in thickness of muscle, blood, and air and thus help in selecting the frequency of the measurement and characteristic waveform of the recorded sensor signal as a function of the beating heart. It is believed that the model assists in assessing the mechanisms responsible for modulation of the return loss signal as a function of either ventricular volume and of the movement of the ventricular wall. Similarly, introduction of an air pocket, as in pneumothorax, would create an impedance change that may be predicted by the model and therefore measurable by a suitable RF device.

Figure 8:
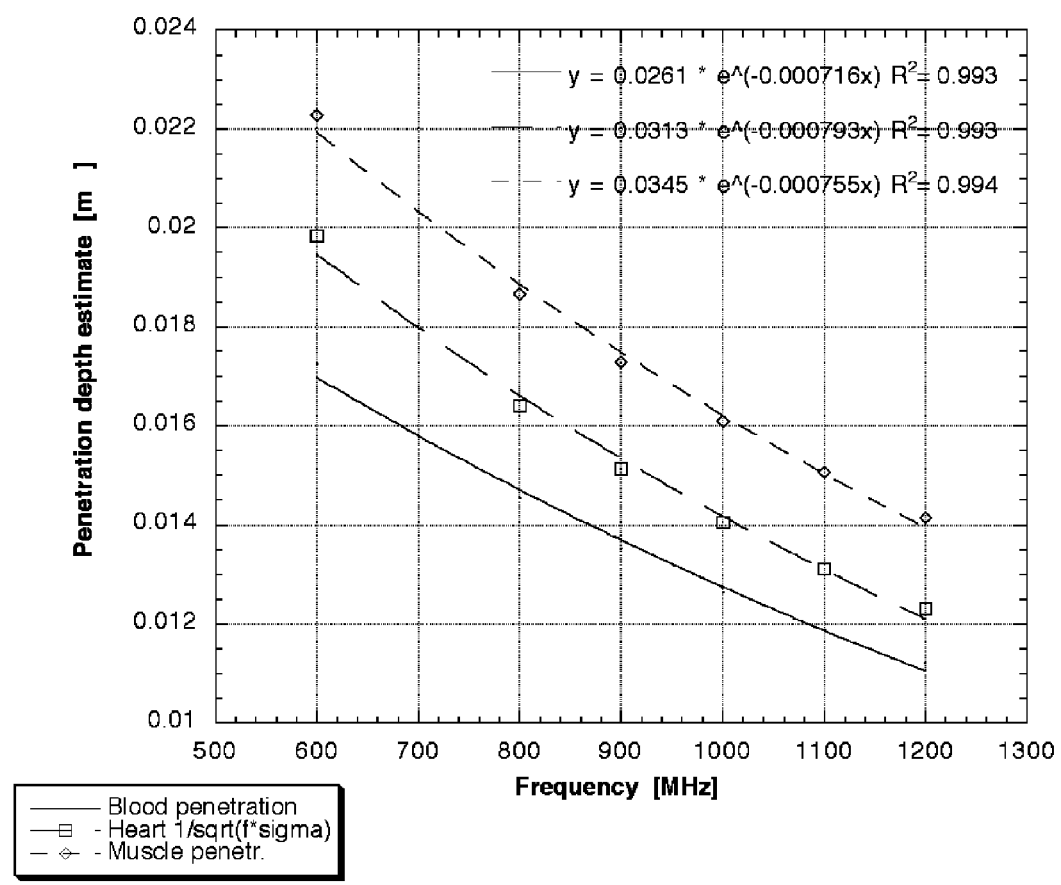
FIG. 8 illustrates an estimated depth of penetration of an EM wave in various tissues in accordance with one embodiment of the present invention.

Selection of the working frequency impacts the depth of penetration of the RF radiation into the tissues. FIG. 8 is a schematic of the anticipated depth of penetration with the range of frequencies of interest to this project, based on the literature data. The model assumes that the body is represented by a sequence of layers, corresponding to chest wall, heart muscle, blood and bone. Based on a lumped parameter model of a transmission line, complex electrical impedance was calculated for each layer, and an impedance change (reflection) was determined at each interlayer interface. According to this model, each layer, corresponding to different tissue forms a load for the EM wave traveling through the immediately preceding layer of tissue, and calculations are completed iteratively for all the layers of tissues, over a range of frequencies and dimensions.

The reflection coefficient in a lossy terminated transmission line is given by:

$$\rho = (Z_1 - Z_0)/(Z_1 + Z_0)$$

where $Z_1$ is the complex impedance of the load, and $Z_0$ is the complex input impedance "looking into" the line. For example, for the first layer, $Z_1$ is the characteristic impedance of the chest wall, which is assumed to be a 2 cm thick layer with dielectric properties corresponding to those of the muscle, bone and fat in 1:1:1 proportion. The input impedance at each interface can be computed using the formula:

$$Z_{in} = Z_0 * [(Z_1 + j*Z_0 * \tan h(\lambda 1))/Z_0 + j*Z_1 * \tan h(\lambda 1)]$$

and $$\tan h(\lambda 1) = (\sin h(\alpha 1)*\cos h(\beta 1) + j*\cos h(\alpha 1)*\sin h(\beta 1))/(\cos h(\alpha 1)*\cos h(\beta x) + j*\sin h(\alpha 1)*\sin h(\beta)1))$$

Where $\beta$ = is the phase constant parameter representing lossy (imaginary) part of the complex propagation constant, $\lambda = \alpha + j\beta$ and $\alpha$ is the attenuation constant. The intrinsic impedance is calculated from the formula:

$$Z_i = SQRT(\mu/\epsilon_r \epsilon_0) * [1/SQRT(1 - j\sigma/\omega \epsilon_r \epsilon_0))]$$

Figure 9:
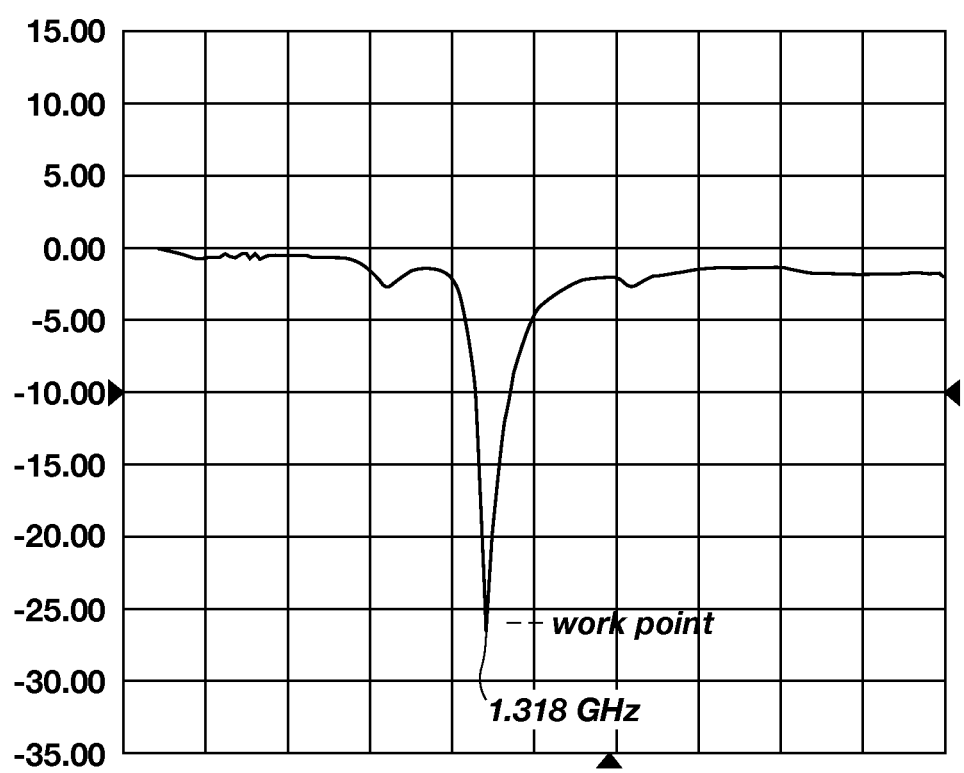
FIG. 9 is an illustration of a frequency tuning sweep and resulting work point in accordance with one embodiment of the present invention.

FIG. 9 is an illustration of a frequency tuning sweep and resulting work point in accordance with one embodiment of the present invention.

Animal Studies

In the course of developing certain embodiments of the present invention, animal testing was conducted to establish meteorological correlation between the measured sensor signal and the stroke volume/cardiac output tests that are impossible, or at best extremely dangerous to perform on human subjects. The animal studies included (i) measurements of cardiac output in the pulmonary artery during hemorrhage, and (ii) measurements of cardiac output using the device described herein as a function of blood loss during controlled hemorrhage and in correlation with the Pulmonary Artery Flow ("PAF"). Sensor readings were recorded during: (i) a control period prior to hemorrhage, (ii) bleeding and re-infusion of blood at a rate of 100 ml/min, up to approximately thirty-three percent of the estimated blood volume of the animal, and (iii) terminal bleeding. The following experimental variables were continuously recorded in a personal computer: (i) ECG using 3-lead standard ECG configuration, (ii) breathing, (iii) sensor output, AC-coupled, (iv) sensor output, DC-coupled, (v) PA flow, instantaneous, (vi) PA flow, average, and (vii) frequency (i.e., the optimized maximum return loss frequency).

In order to separate the breathing-related baseline variations, selected segments of data are digitally filtered. In one aspect of the invention, the sensor output signal contains two components: an additive, breathing and motion-modulated baseline at breathing and motion-artifact frequencies, and the stroke volume-related signal at heart beat frequency. The separation of these components is performed in the frequency domain, and is followed by subsequent interpretation of the filtered signal in time domain.

Generally speaking, the digital filtering discussed herein includes the following steps: (i) calculating the FFT of the selected data segments, (ii) plotting the power spectrum, (iii) dividing the power spectrum of the signal into two separate spectra containing the breathing-related and (separately) the heart-beat-related frequency components of the original signal, (iv) re-creating the heart-related and breathing-related waveforms using inverse FFT function, and (v) plotting the peak amplitudes of the sensor signal versus the corresponding peak amplitudes of the PA flow or volume bled/re-infused.

In one aspect of the invention, the frequency bandwidth used for the analysis is 3 Hz (adjustable), and the breathing rate separation frequency is 0.75 Hz, or 25% of frequency bandwidth. This routine resulted in zero-average signals that showed multiplicative (amplitude) modulation by breathing. This digital filter was implemented in MatLab and the calculations were performed off-line. However, this filter routine can be implemented for processing of the RF sensor data in real time on an embedded platform. This method of filtering the baseline drift and its additive contribution to the sensor signal is not adaptive and does not account for inter-subject variability. However, it provides a simple and effective method of separating the breathing and low frequency motion interferants. In dynamic situations, when static selection of filtration boundaries is not possible, the limits are adjusted dynamically as a function of heart and breathing frequencies.

Figure 10:
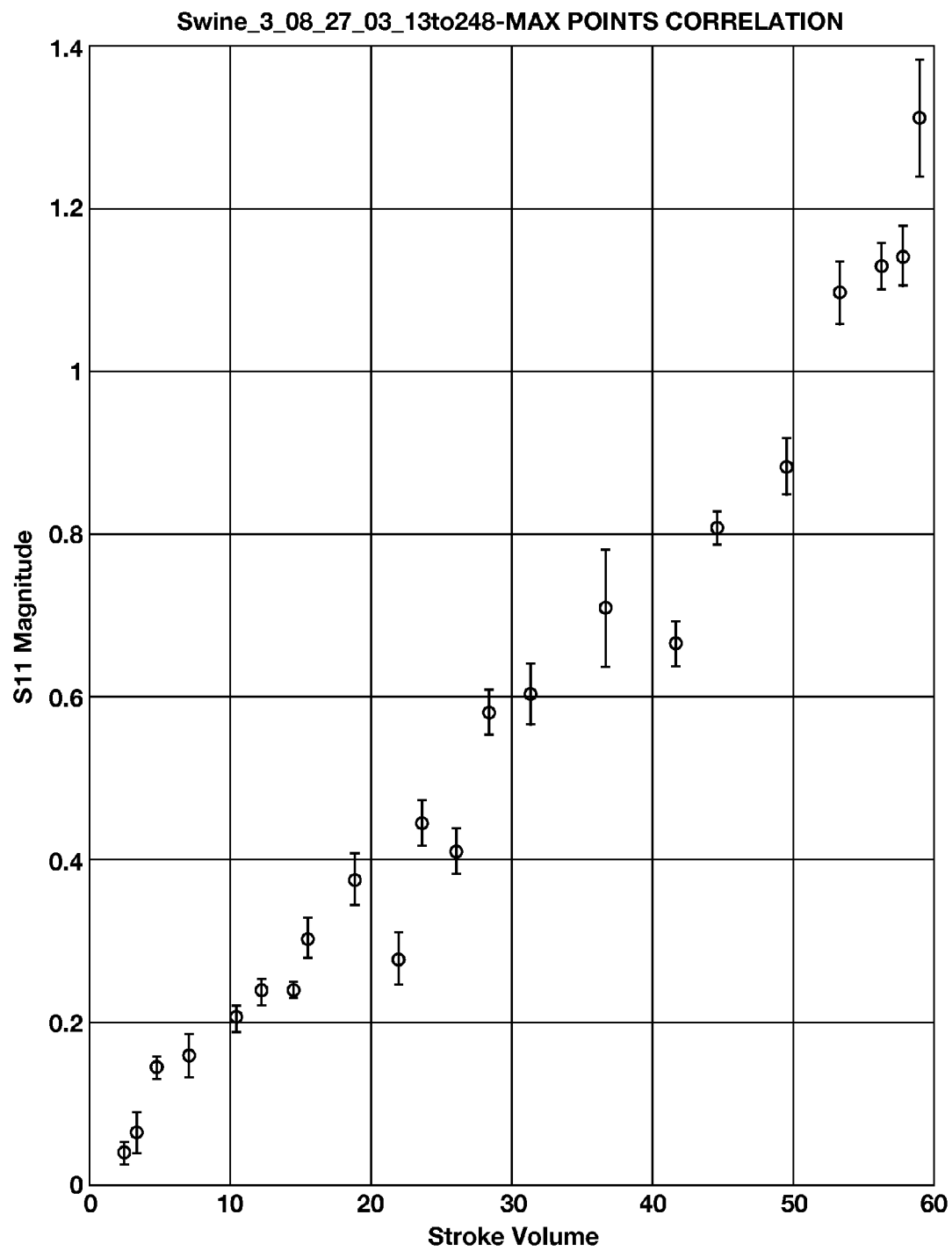
FIG. 10 shows a data plot of the sensor magnitude versus pulmonary artery stroke volume from experiment SW3 in accordance with one embodiment of the present invention.

FIG. 10 shows one implementation of the above-described filter using MatLab data processing software for a selected data segment. Specifically, FIG. 10 shows a data plot of the sensor magnitude versus pulmonary artery stroke volume from experiment SW3 in accordance with one embodiment of the present invention.

Figure 11:
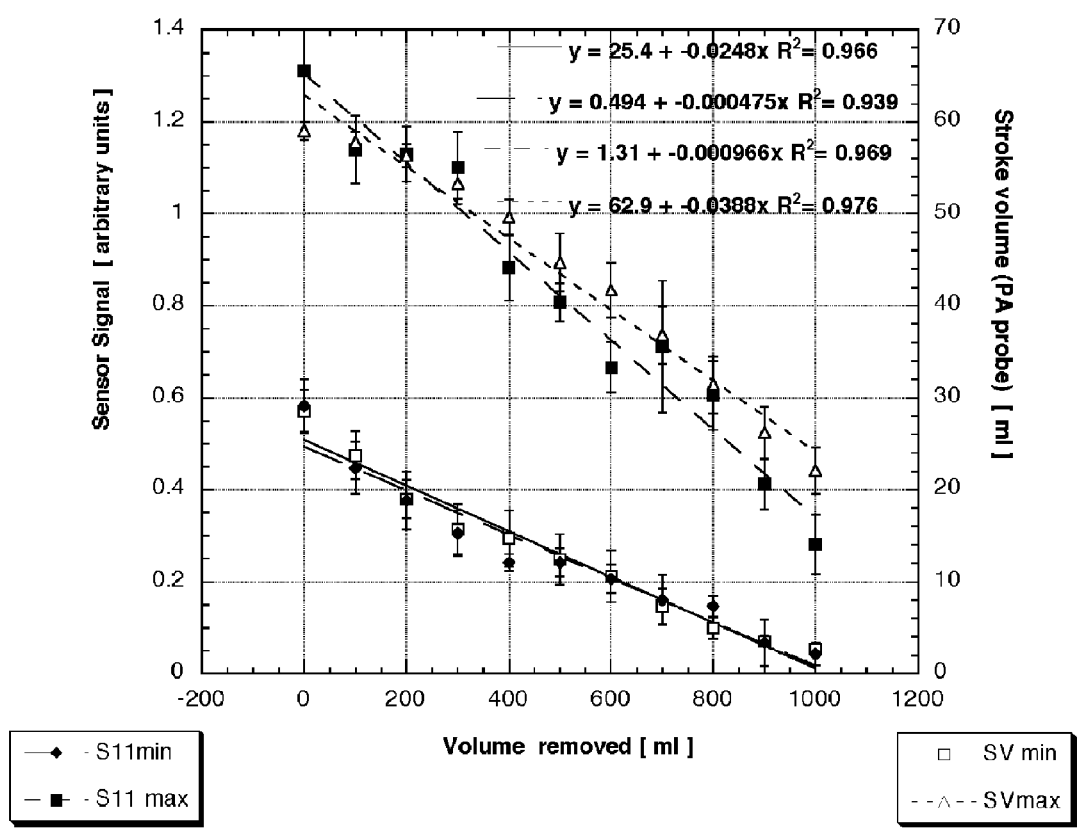
FIG. 11 shows the bleed summary of experiment SW3 in accordance with one embodiment of the present invention.
Figure 12A:
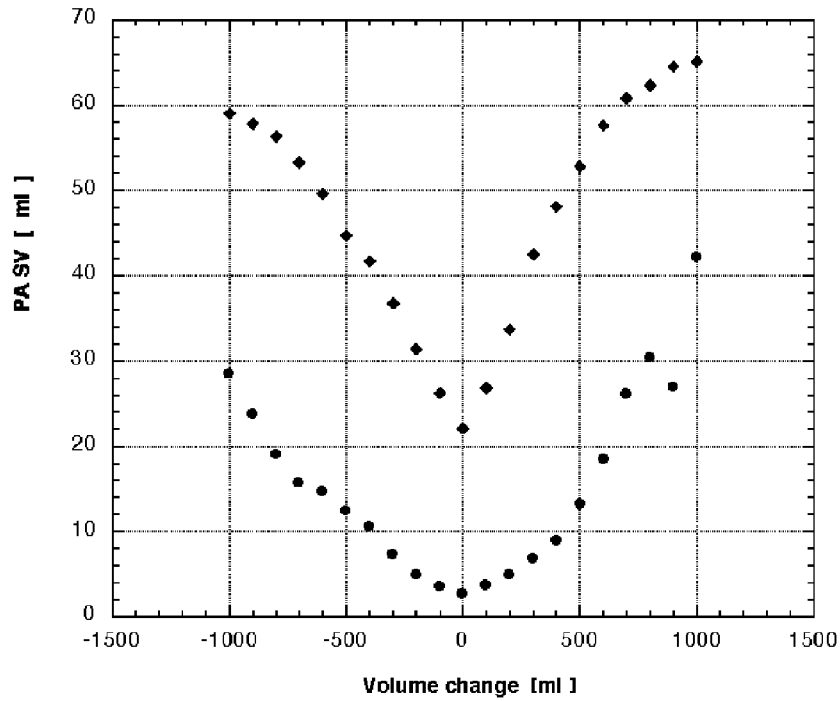
FIG. 12 shows a comparison of stroke volume derived from PA flow test and sensor signal during full bleed and re-infusion during experiment SW3 in accordance with one embodiment of the present invention.
Figure 12B:
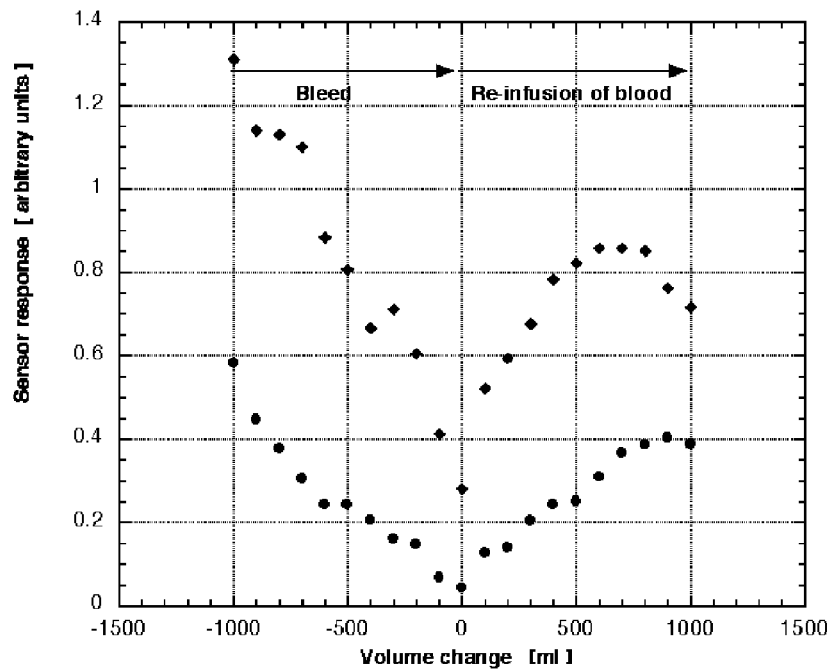
Figure 13:
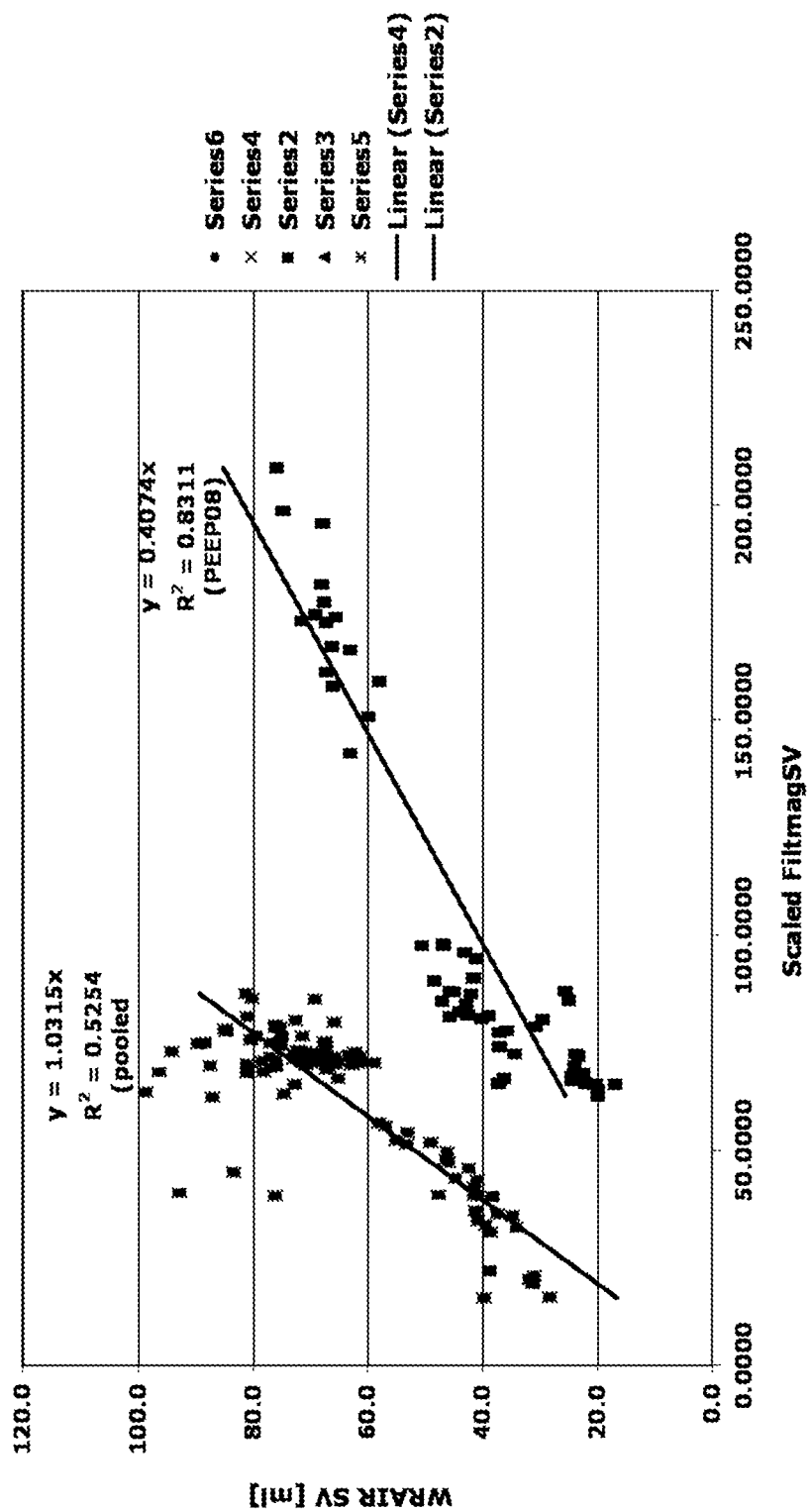
FIG. 13 shows calibration lines for PEEP experiments 4, 6, 13, and 14 in accordance with one embodiment of the present invention.

FIG. 11 provides a summary data from the bleed experiment in SW3 experiment. High correlation between the returned RF device signal with bled volume is practically the same as for the pulmonary artery stroke volume signal, indicating that the RF device can become a non-invasive, simple to use diagnostic tool for detection of hemorrhage. FIG. 12 (upper panel) shows a bleed re-infusion cycle in the animal of SW3. Stroke volume derived by integrating PA instantaneous flow is plotted versus blood loss/gain. From the same data record, the bottom panel shows the sensor signal plotted similarly. FIG. 13 provides correlation graph for pooled unsealed PEEP08 and PEEP14 data. The correlation coefficient, R=0.9116, indicated a strong correlation between stroke volume derived from COTB measurements, and that from the RF sensor signal.

The foregoing detailed description describes the invention with reference to specific exemplary embodiments. However, it will be appreciated that various modifications and changes can be made without departing from the scope of the present invention as set forth in the appended claims. The detailed description and accompanying drawings are to be regarded as merely illustrative, rather than as restrictive, and all such modifications or changes, if any, are intended to fall within the scope of the present invention as described and set forth herein.

More specifically, while illustrative exemplary embodiments of the invention have been described herein, the present invention is not limited to these embodiments, but includes any and all embodiments having modifications, omissions, combinations (e.g., of aspects across various embodiments), adaptations and/or alterations as would be appreciated by those in the art based on the foregoing detailed description. The limitations in the claims are to be interpreted broadly based on the language employed in the claims and not limited to examples described in the foregoing detailed description or during the prosecution of the application, which examples are to be construed as non-exclusive. For example, in the present disclosure, the term "preferably" is non-exclusive where it is intended to mean "preferably, but not limited to." Any steps recited in any method or process claims may be executed in any order and are not limited to the order presented in the claims. Means-plus-function or step-plus-function limitations will only be employed where for a specific claim limitation all of the following conditions are present in that limitation: a) "means for" or "step for" is expressly recited; and b) a corresponding function is expressly recited. The structure, material or acts that support the means-plus function are expressly recited in the description herein. Accordingly, the scope of the invention should be determined solely by the appended claims and their legal equivalents, rather than by the descriptions and examples given above.

What is claimed and desired to be secured by Letters Patent is:

1. A system for measuring cardiac parameters of the heart of a person, comprising:
    a device comprising a housing containing a signal generator coupled to an antenna and a dielectric material disposed about the antenna, wherein said device is adapted to repeatedly generate a sweep of radio frequency signals at a plurality of frequencies and direct said signals towards the heart of the person and measure magnitudes of signals returned off the heart of the person; and
    a processor contained within said housing, said processor being adapted to compare magnitudes of the radio frequency signals propagated into the heart of the person and magnitudes of the signals returned from the heart to determine return loss values for each of the radio frequency signals,
    said processor being adapted to determine a maximum return loss value for each sweep of radio frequency signals and estimate a change in the amplitude of motion of a portion of a wall of the heart based on changes in the maximum return loss values.

2. The system of claim 1, wherein said processor is further adapted to calculate the cardiac output of the person; and further comprising a display disposed about the device adapted to display the measured signals and that can be calibrated to display the estimated stroke volume of the person.

3. The system of claim 2, wherein said processor is further adapted to calculate the cardiac parameters of the person based on an estimated stroke volume of the person.

4. The system of claim 1, wherein said device is adapted to generate a signal at a frequency and magnitude having a determined maximum return loss value into the portion of the heart and receive a portion of the signal propagated into the portion of the heart.

5. The system of claim 1, wherein the dielectric material is selected from the group consisting of ceramics, glass, liquids, gels and polymeric materials.

6. The system of claim 3, wherein said processor is further adapted to estimate the stroke volume of the heart based on a change of the amplitude of motion of the portion of the wall of the heart.

7. The system of claim 6, wherein said processor is adapted to estimate the timing of a QRS complex of the heart based on the change of the amplitude of motion of the portion of the wall of the heart.

8. The system of claim 6, wherein said processor is further adapted to estimate the timing a QRS complex of the heart based on a change of a frequency of a signal having the maximum return loss value.

9. The system of claim 1, wherein the dielectric material has a predetermined thickness and a predetermined dielectric constant such that a substantial portion of a near field component of the radio frequency signals propagated towards the heart of the person is contained within said dielectric material.

10. The system of claim 1, wherein the dielectric material has a predetermined thickness and a predetermined dielectric constant such that substantially an entire near field component of the radio frequency signals propagated towards the heart of the person is contained within said dielectric material.

11. A method for measuring cardiac parameters of a person, comprising:
    (a) placing a device about the center of the chest of the person at the mid-sternum position, said device comprising a signal generator coupled to an antenna, said antenna having a dielectric material disposed about the exterior of the antenna;
    (b) propagating a first signal having a predetermined frequency towards the heart of the person;
    (c) receiving and measuring a portion of the first signal returned from the heart of the person with the device;
    (d) comparing the magnitude of the first signal propagated into the heart of the person to the magnitude of the portion of the first signal returned from the heart of the person and calculating a return loss of the signal;
    (e) repeating steps (b) through (d) for a plurality of signals while incrementally varying the frequency of the additional signals over a predetermined frequency range; and
    (f) determining a maximum return loss value of the signals propagated into the heart of the person over the predetermined frequency range: and
    (g) repeating steps (b) through (f) and estimating a change in the amplitude of motion of a portion of a wall of the heart based on changes in maximum return loss values.

12. The method of claim 11, wherein the first signal and the plurality of signals comprise a radio frequency signal.

13. The method of claim 11, wherein the dielectric material is selected from the group consisting of ceramics, glass, liquids, gels and other polymeric materials.

14. The method of claim 11, further comprising estimating impedance of the tissues inside the thorax of the person.

15. The method of claim 14, further comprising estimating a change in the impedance of the tissues inside the thorax of the person.

16. The method of claim 15, further comprising estimating a stroke volume of the heart based on the change in the impedance of the tissues inside the thorax of person.

17. The method of claim 15, further comprising determining the timing of a QRS complex of the heart based on a change in the magnitude of the maximum return loss values.

18. The method of claim 15, further comprising determining the timing of a QRS complex of the heart based on a change in frequency of the maximum return loss values.

19. The method of claim 11, wherein the portion of the heart comprises a right ventricle of the heart.

20. A method for measuring cardiac output of a person, comprising:
- (a) placing a hand-held device about the person, said device comprising a radio frequency signal generator coupled to an antenna;
- (b) propagating a sweep of signals having a constant magnitude into a portion of the heart of the person wherein each signal of the sweep of signals has a different frequency;
- (c) receiving and measuring a portion of the sweep of signals returned from the heart of the person with the device; and
- (d) determining, out of the sweep of signals returned from the heart of the person, the signal of maximum return loss;
- (e) repeatedly generating sweeps of signals having a constant magnitude at a plurality of frequencies and directing said signals towards the heart of the person and measuring magnitudes of the signals returned off the heart of the person to determine a return loss of each signal;
- (f) determining a maximum return loss value for each sweep of radio frequency signals; and
- (g) estimating a change in the amplitude of motion of a portion of a wall of the heart based on changes in maximum return loss values.

21. A method for estimating a volume of fluid within the thorax of a person, comprising:
- (a) placing a device about the chest of the person, said device comprising a signal generator coupled to an antenna, said antenna having a dielectric material disposed about the exterior of the antenna;
- (b) propagating a first signal having a predetermined frequency towards the thorax of the person;
- (c) receiving and measuring a portion of the first signal returned from the thorax of the person with the device;
- (d) comparing the magnitude of the first signal propagated into the thorax of the person to the magnitude of the portion of the first signal returned from the thorax of the person and calculating a return loss of the signal;
- (e) repeating steps (b) through (d) for a plurality of signals while incrementally varying the frequency of the additional signals over a predetermined frequency range; and
- (f) determining a maximum return loss value of the signals propagated into the thorax of the person over the predetermined frequency range: and
- (g) repeating steps (b) through (f) and estimating a change in the amplitude of motion of a portion of a wall of an organ within the thorax based on changes in maximum return loss values.

22. A system for estimating a volume of fluid within the thorax of a person, comprising:
- a device comprising a housing containing a signal generator coupled to an antenna and a dielectric material disposed about the antenna, wherein said device is adapted to repeatedly generate a sweep of radio frequency signals at a plurality of frequencies and direct said signals towards the thorax of the person and measure magnitudes of signals returned off the thorax of the person;
- a processor contained within said housing, said processor being adapted to compare magnitudes of the radio frequency signals propagated into the thorax of the person and magnitudes of the signals returned from the thorax to determine return loss values for each of the radio frequency signals; and
- said processor being adapted to determine a maximum return loss value for each sweep of radio frequency signals and estimate a change in the amplitude of motion of a portion of a wall of an organ within the thorax based on changes in the maximum return loss values.

23. A method for estimating a volume of fluid within the thorax of a person, comprising:
- (a) placing a hand-held device about a person, said device comprising a radio frequency signal generator coupled to an antenna;
- (b) propagating a sweep of signals having a constant magnitude into a portion of the thorax of the person wherein each signal of the sweep of signals has a different frequency;
- (c) receiving and measuring a portion of the sweep of signals returned from the thorax of the person with the device; and
- (d) determining, out of the sweep of signals returned from the thorax of the person, the signal of maximum return loss;
- (e) repeatedly generating sweeps of signals having a constant magnitude at a plurality of frequencies and directing said signals towards the thorax of the person and measuring magnitudes of the signals returned off the thorax of the person to determine a return loss of each signal;
- (f) determining a maximum return loss value for each sweep of radio frequency signals; and
- (g) estimating a change in the amplitude of motion of a portion of a wall of an organ within the thorax based on changes in maximum return loss values.

* * * * *